US007892813B2

(12) United States Patent
Young et al.

(10) Patent No.: US 7,892,813 B2
(45) Date of Patent: Feb. 22, 2011

(54) **FUNGAL ENDOPHYTES OF *ELYMUS CANADENSIS***

(75) Inventors: Carolyn Young, Ardmore, OK (US); Andy Hopkins, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 244 days.

(21) Appl. No.: 12/029,797

(22) Filed: Feb. 12, 2008

(65) Prior Publication Data

US 2008/0229441 A1    Sep. 18, 2008

Related U.S. Application Data

(60) Provisional application No. 60/889,480, filed on Feb. 12, 2007.

(51) Int. Cl.
*C12N 1/00*    (2006.01)
(52) U.S. Cl. .................................................. 435/254.1
(58) Field of Classification Search ............... 435/254.1
See application file for complete search history.

(56) References Cited

U.S. PATENT DOCUMENTS

| 5,723,720 | A | 3/1998 | Brede et al. ................. 800/200 |
| 5,880,343 | A | 3/1999 | Hiruma et al. ............... 800/200 |
| 6,111,170 | A * | 8/2000 | Latch et al. .................. 800/320 |
| 6,815,591 | B1 | 11/2004 | Hignight et al. ............. 800/320 |
| 7,232,565 | B2 | 6/2007 | Henson et al. .............. 424/93.5 |
| 2005/0150024 | A1 | 7/2005 | West et al. .................. 424/93.5 |
| 2006/0121593 | A1 | 6/2006 | Christensen et al. | |
| 2006/0150273 | A1 | 7/2006 | Tapper et al. | |
| 2008/0207451 | A1 | 8/2008 | Imada et al. ................. 504/117 |

FOREIGN PATENT DOCUMENTS

| CA | 2500144 | 4/2004 |
| EP | 0 836 378 | 8/2001 |
| EP | 1 142 986 | 10/2001 |
| JP | 05317092 | 3/1993 |
| WO | WO 90/13224 | 11/1990 |
| WO | WO 99/29177 | 6/1999 |
| WO | WO 02/13616 | 2/2002 |
| WO | WO 2004/106487 | 12/2004 |
| WO | WO 2005/003328 | 1/2005 |
| WO | WO 2007/107000 | 9/2007 |

OTHER PUBLICATIONS

Clay et al., "Evolutionary Origins and Ecological Consequences of Endophyte Symbiosis with Grasses", Oct. 2002, vol. 160, pp. S99-S127, The University of Chicago.

Craven et al., "Multigene Phylogeny of Epichloe Species, Fungal Symbionts of Grasses", 2001, Ann. Missouri Bot. Gard. 88:14-34.
Fleetwood et al., "A Complex Ergovaline Gene Cluster in Epichloe Endophytes of Grasses", Apr. 2007, Applied and Environmental Microbiology, vol. 73, No. 8, pp. 2571-2579.
Panaccione et al., "Biochemical Outcome of Blocking the Ergot Alkaloid Pathway of a Grass Endophyte", 2003, J. Agric. Food Chem., 51, pp. 6429-6437.
Panaccione, "Origins and significance of ergot alkaloid diversity in fungi", 2005, FEMS Microbiology Letters 251, pp. 9-17.
Spiering et al., "Gene Clusters for Insecticidal Loline Alkaloids in the Grass-Endophytic Fungus Neotyphodium uncinatum", Mar. 2005, Genetics 169, pp. 1403-1414.
Tanaka et al., "A symbiosis expressed non-ribosomal peptide synthetase from a mutualistic fungal endophyte of perennial ryegrass confers protection to the symbiotum from insect herbivory", 2005, Molecular Microbiology, 47(4), pp. 1036-1050.
Young et al., "A complex gene cluster for indole-diterpene biosynthesis in the grass endophyte Neotyphodium lolii", 2006, Fungal Genetics and Biology 43, p. 679-693.
Bouton et al., "Reinfection of tall fescue cultivars with non-ergot alkaloid-producing endophytes," *Agronomy Journal*, 94(3):567-574, 2002.
Brem et al., "Epichloe grass endophytes increase herbivore resistance in the woodland grass Brachypodium sylvaticum," *Oecologia*, 126:522-530, 2001.
Craven et al., "Multigene phylogeny of Epichloe species, fungal symbionts of grasses," *Annals of the Missouri Botanical Garden*, 88(1):14-34, 2001.
Geneseq Accession No. AAA94774, Jan. 19, 2001.
Geneseq Accession No. AAZ22530, dated Dec. 2, 1999.
Geneseq Accession No. ADQ74839, dated Oct. 7, 2004.
Leuchtmann et al., "Different levels of protective alkaloids in grasses with stroma-forming and seed-transmitting Epichloe/Neotyphodium endophytes," *Journal of Chemical Ecology*, 26(4):1025-1036, 2000.
Li et al., "A new species of Epichloe symbiotic with Chinese grasses," *Mycologia*, 98(4):560-570, 2006.
Tintjer et al., "Grass-herbivore interactions altered by strains of a native endophyte," *New Phytologist*, 170:513-521, 2006.

* cited by examiner

*Primary Examiner*—Medina A. Ibrahim
*Assistant Examiner*—Keith O. Robinson
(74) *Attorney, Agent, or Firm*—Steven P. Rhines, Esq.; SNR Denton US LLP

(57) ABSTRACT

The invention provides an isolated culture of a *Neotyphodium* endophyte of an *Elymus canadensis* host plant, wherein the endophyte reproduces asexually and enhances the agronomic characteristics of the host plant. Methods for inoculating the host plant with the endophyte, for propagating the host-endophyte combination, and for detecting the presence of the endophyte and of its metabolites within a host plant are also described.

18 Claims, 6 Drawing Sheets

FIG 2

SEQUENCE LISTING

```
<160> NUMBER OF SEQ ID NOS: 77

<210> SEQ ID NO 1
<211> LENGTH: 591
<212> TYPE: DNA
<213> ORGANISM: Epichloe sp.

<400> SEQUENCE: 1
gtaacaaggt ctccgttggt gaaccagcgg agggatcatt accgagtttt acaccccaa      60 accctgtga  acctatacct actgttgcct cggcgggcac ggccgcggac gcccctcgc    120 gggggcaccg gggccaggcg cccgccggag gacccaaacc cttctgtatt ttctaacgta   180
cgtctgagtg gatttaatat caaatgaatc aaaactttca acaacggatc tcttggttct   240
ggcatcgatg aagaacgcag cgaaatgcga taagtaatgc gaattgcaga attcagtgaa   300
tcatcgaatc tttgaacgca cattgcgccc gccagtattc tggcgggcat gcctgttcga   360
gcgtcatttc aaccctcaag cccgctgcgc gcttggtgtt ggggaccggc cggcccgcct   420
cgcggcggcg gccgcccctg aaatgaattg gcggtctcgt cgcagcctcc cttgcgtagt   480
aacataccac ctcgcaaccg ggagcgcggc gcggccactg ccgtaaaacg cccaacttct   540
ccaagagttg acctcgaatc aggtaggact acccgctgaa cttaagcata t             591

<210> SEQ ID NO 2
<211> LENGTH: 21
<212> TYPE: DNA
<213> ORGANISM: Artificial
<220> FEATURE:
<223> OTHER INFORMATION: Synthetic Primer

<400> SEQUENCE: 2
gggtaaggac gaaaagactc a                                               21

<210> SEQ ID NO 3
<211> LENGTH: 21
<212> TYPE: DNA
<213> ORGANISM: Artificial
<220> FEATURE:
<223> OTHER INFORMATION: Synthetic primer

<400> SEQUENCE: 3
cggcagcgat aatcaggata g                                               21
```

<210> SEQ ID NO 4
<211> LENGTH: 20
<212> TYPE: DNA
<213> ORGANISM: Artificial
<220> FEATURE:
<223> OTHER INFORMATION: Synthetic Primer

<400> SEQUENCE: 4
tcctccgctt attgatatgc                                          20

<210> SEQ ID NO 5
<211> LENGTH: 22
<212> TYPE: DNA
<213> ORGANISM: Artificial
<220> FEATURE:
<223> OTHER INFORMATION: Synthetic Primer

<400> SEQUENCE: 5
ggaagtaaaa gtcgtaacaa gg                                       22

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
gagaaaatgc gtgagattgt                                          20

<210> SEQ ID NO 7
<211> LENGTH: 20
<212> TYPE: DNA
<213> ORGANISM: Artificial
<220> FEATURE:
<223> OTHER INFORMATION: Synthetic primer

<400> SEQUENCE: 7
ctggtcaacc agctcagcac                                          20

<210> SEQ ID NO 8
<211> LENGTH: 695
<212> TYPE: DNA
<213> ORGANISM: Neotyphodium sp.

<400> SEQUENCE: 8
aagttcaacc tctctgtttg tcttggggac cccctcctcg acgcgttccg gtgttgagcc    60
cctgatttcg tacccgccg agcccggcca cgacgtgcac gcccaacgaa cagtcgtgat    120
gagaggcgga ccgagacaaa atgaacgaat gcggtattcg agaactgtag ctgacctgtt    180
tctttccctc ttttccctc taggttcatc ttcaaaccgg tcagtgcgta agtgacaaat    240
ccgccgacct cgaacgacag gcacaaacag catgaaaaac tcacattcat ttgggcaggg    300
taaccaaatt ggtgctgctt tctggcagac catctctggc gagcacggcc tcgacagcaa    360
tggtgtgtac aatggtacct ccgagctcca gcttgagcgt atgagtgtct acttcaacga    420
ggtaagtctt cataatctaa agtctccatt gagctacata cataccgccc cggagatgag    480
acggaaagag aacgagagaa aaagtgtcat catgctcatc catgtgacag gcttctggca    540
acaagtatgt tcctcgcgct gtcctcgtcg atccgagcc tggtaccatg gatgcagtcc    600
gtgccggtcc cttcggtcag ctttccgtc ctgacaactt cgtcttcggt cagtctggtg    660

```
ctggcaacaa ctgggccaag ggtcactaca ctgag                              695
```

<210> SEQ ID NO 9
<211> LENGTH: 680
<212> TYPE: DNA
<213> ORGANISM: Neotyphodium sp.

<400> SEQUENCE: 9

```
aagttcaacc tctctgtttg tcttggggac cccctcctcg acgcgttccg gtgttgagcc    60
cctgatttcg taccccgccg agcccggcca cgacgtgcac gcccaacgaa cagtcgtgat   120
gagaggctga ccgagacaaa atgaacgaat gcggtattcg agaactgtag ctgacctgtt   180
tctttccctc ttttcccctc taggttcatc ttcaaaccgg tcagtgcgta agtgacaaat   240
ccgccgacct cgaacgacag gcacaaacag catgaaaaac tcacattcat ttgggcaggg   300
taaccaaatt ggtgctgctt tctggcagac catctctggc gagcacggcc tcgacagcaa   360
tggtgtgtac aatggtacct ccgagctcca gcttgagcgt atgagtgtct acttcaacga   420
ggtaagtctt cataatctaa agtctccatt gagctacata cataccgccc cggagatgag   480
acggaaagag aacgagagaa aaagtgtcat catgctcatc catgtgacag gcttctggca   540
acaagtatgt tcctcgcgct gtcctcgtcg atctcgagcc tggtaccatg gatgcagtcc   600
gtgccggtcc cttcggtcag cttttccgtc ctgacaactt cgtcttcggt cagtctggtg   660
ctggcaacaa ctgggccaag                                              680
```

<210> SEQ ID NO 10
<211> LENGTH: 672
<212> TYPE: DNA
<213> ORGANISM: Neotyphodium sp.

<400> SEQUENCE: 10

```
aagtttaacc gctctgtttg tcttggggac cccctcctcg acgcgttccg gtgttgagcc    60
cctgatttcg taccccgccg agcccggcca cgacgtgcac gcccaatgga caagtcgtga   120
tgagaggcgg accgagacaa aaaattaatg attgcggtat tcgagaactg ttagctgacc   180
tttttcttcc cctctaggtt catcttcaaa ccggtcagtg cgtaagtgac aaatccgccg   240
acctagaacg acgggcacaa ataacatgaa aaactcacat ttatttgggc agggtaacca   300
aattggtgct gctttctggc agaccatctc tggcgagcac ggcctcgaca gcaatggtgt   360
gtacaatggt acctccgagc tccagctgga gcgtatgagt gtctacttca acgaggtaag   420
tcttcataat ctaaagtctc cattgagcta cataccgccc tggagatgag acggaaagag   480
aacgaaagaa aaagtgtcat catatgctaa tctatgtgac aggcttctgg caacaagtat   540
gttcctcgcg ctgtcctcgt cgatctcgag cctggtacca tggatgcagt ccgtgccggt   600
cccttcggtc agcttttccg tcccgacaac ttcgtcttcg gtcagtctgg tgctggcaac   660
aactgggcca ag                                                      672
```

<210> SEQ ID NO 11
<211> LENGTH: 695
<212> TYPE: DNA
<213> ORGANISM: Neotyphodium sp.

<400> SEQUENCE: 11

```
aagttcaacc tctctgtttg tcttggggac cccctcctcg acgcgttccg gtgttgagcc    60
cctgatttcg taccccgccg agcccggcca cgacgtgcac gcccaacgaa cagtcgtgat   120
gagaggcgga ccgagacaaa atgaacgaat gcggtattcg agaactgtag ctgacctgtt   180
```

```
tctttccctc ttttccctc taggttcatc ttcaaaccgg tcagtgcgta agtgacaaat      240
ccgccgacct cgaacgacag gcacaaacag catgaaaaac tcacattcat ttgggcaggg      300
taaccaaatt ggtgctgctt tctggcagac catctctggc gagcacggcc tcgacagcaa      360
tggtgtgtac aatggtacct ccgagctcca gcttgagcgt atgagtgtct acttcaacga      420
ggtaagtctt cataatctaa agtctccatt gagctacata caccgcccc ggagatgag       480 acggaaagag aacgagagaa aaagtgtcat catgctcatc catgtgacag gcttctggca      540
acaagtatgt tcctcgcgct gtcctcgtcg atctcgagcc tggtaccatg gatgcagtcc      600
gtgccggtcc cttcggtcag cttttccgtc ctgacaactt cgtcttcggt cagtctggtg      660
ctggcaacaa ctgggccaag ggtcactaca ctgag                                 695

<210> SEQ ID NO 12
<211> LENGTH: 687
<212> TYPE: DNA
<213> ORGANISM: Neotyphodium

<400> SEQUENCE: 12
aagtttaacc gctctgtttg tcttggggac cccctcctcg acgcgttccg gtgttgagcc      60
cctgatttcg taccccgccg agcccggcca cgacgtgcac gcccaatgga caagtcgtga     120
tgagaggcgg accgagacaa aaaattaatg attgcggtat tcgagaactg ttagctgacc     180
tttttcttcc cctctaggtt catcttcaaa ccggtcagtg cgtaagtgac aaatccgccg     240
acctagaacg acgggcacaa ataacatgaa aaactcacat ttatttgggc agggtaacca     300
aattggtgct gctttctggc agaccatctc tggcgagcac ggcctcgaca gcaatggtgt     360
gtacaatggt acctccgagc tccagctgga gcgtatgagt gtctacttca acgaggtaag     420
tcttcataat ctaaagtctc cattgagcta cataccgccc tggagatgag acggaaagag     480
aacgaaagaa aaagtgtcat catatgctaa tctatgtgac aggcttctgg caacaagtat     540
gttcctcgcg ctgtcctcgt cgatctcgag cctggtacca tggatgcagt ccgtgccggt     600
cccttcggtc agcttttccg tcccgacaac ttcgtcttcg gtcagtctgg tgctggcaac     660
aactgggcca agggtcacta cactgag                                          687

<210> SEQ ID NO 13
<211> LENGTH: 864
<212> TYPE: DNA
<213> ORGANISM: Neotyphodium sp.

<400> SEQUENCE: 13
gggtaaggac gaaagactc acatcaacgt ggtcgttatc gtaagttgac tttgacctgt       60
atcattcgat gtattggata acagttgcta acttgtttgc taacaggggt acgtactgcg     120
aaatatcact cgccgttgcc gaaattcacg tactgactga agcgtagcca cgtcgactct     180
ggcaagtcta ccaccaccgg tcacttgatc taccagtgcg gtggaattga caagcgtacc     240
atcgagaagt tcgagaaggt aatatattct actcctctca cgcataatat ctgatgttca     300
ctcgttgcaa tgcgagcctg ccttgtgtgt cgctttgcaa ccttggtggg caagcaagcg     360
acttgcccgc ccaccaaagc ccctcttttt cgcccgcgat acgaattttt ttttttttc      420 ggtcgcgggg ctcagtctga cttttggtgg ggcacctctc aacccgtcac tggtcttgag     480
ctagaagacg caaacgagag agacatgaca tgacattcgc gtggccccc aaaaaaaatt      540 gtgattaaaa atcactgaca tgccttcgct ctataggaag ccgccgaact cggaaagggt     600
```

```
tctttcaaat atgcgtgggt tcttgacaag ctcaaggccg agcgtgagcg tggtatcacc    660
atcgacattg ccctctggaa gttcgagact cccaagtact atgtcaccgt cattggtaag    720
ccttggtcga tgcattagac tcttcttacc cgatctgcat cattaacgtg catctattag    780
acgctcccgg tcaccgtgat ttcatcaaga acatgattac tggtacttcc caggctgact    840
gcgctatcct gattatcgct gccg                                           864

<210> SEQ ID NO 14
<211> LENGTH: 850
<212> TYPE: DNA
<213> ORGANISM: Neotyphodium sp.

<400> SEQUENCE: 14
gggtaaggac gaaagactc acatcaacgt ggtcgttatc gtaagtttac tttgacctgt      60
atcattcgat gtatcggata acagttgcta acttgtctgc taacaggggt acgtactgcg    120
aaatatcact cgccgttgcc gaaattgacg tactgactga agcgtagcca cgtcgactct    180
ggcaagtcta ccaccaccgg tcacttgatt taccagtgcg gtggaattga caagcgtacc    240
atcgagaagt tcgagaaggt aagatattct tctttcactt cacgcataat atgtgatgtt    300
cactcgttgc aatgcgagcc tgccttgtgt gtcgctttgc aaccttggtg gcaagcaag    360 catctgcccc tcttttcgcc cgcgatacga attttttttt tttttcggt cgcggggctc    420 agtctgactt ttggtggggc acctctctac ccgtcactgg tctaagctag agacgcaaac    480
gagagagaca tgacatggga ttcgcgtggt ctcccaaaaa aaactgtgat gacaaatcac    540
tgacttgcct tcgctctata ggaagccgcc gaactcggaa agggttcttt caaatatgcg    600
tgggttcttg acaagctcaa ggccgagcgt gagcgtggta tcaccatcga cattgccctc    660
tggaagttcg agactcccaa gtactatgtc accgtcattg gtaagccttg gtcgacacac    720
tagactctta tcaacccgat ctgtatcatt aacgtgcatc ttttagacgc tcccggtcac    780
cgtgatttca tcaagaacat gattactggt acttcccagg ctgactgcgc tatcctgatt    840
atcgctgccg                                                           850

<210> SEQ ID NO 15
<211> LENGTH: 808
<212> TYPE: DNA
<213> ORGANISM: Epichloe elymi

<400> SEQUENCE: 15
catcaacgtg gtcgttatcg taagtttact ttgacctgta tcattcgatg tatcggataa     60
cagttgctaa cttgtctgct aacaggggta cgtactgcga aatatcactc gccgttgccg    120
aaattgacgt actgactgaa gcgtagccac gtcgactctg gcaagtctac caccaccggt    180
cacttgattt accagtgcgg tggaattgac aagcgtacca tcgagaagtt cgagaaggta    240
agatattctt ctttcacttc acgcataata tgtgatgttc actcgttgca atgcgagcct    300
gccttgtgtg tcgctttgca accttggtgg caagcaagc atctgcccct cttttcgccc    360
gcgatacgaa ttttttttt tttttcggtc gcggggctca gtctgacttt tggtggggca    420
cctctctacc cgtcactggt ctaagctaga gacgcaaacg agagagacat gacatgggat    480
tcgcgtggcc tcccaaaaaa aactgtgatg acaaatcact gacttgcctt cgctctatag    540
gaagccgccg aactcggaaa gggttctttc aaatatgcgt gggttcttga caagctcaag    600
gccgagcgtg agcgtggtat caccatcgac attgccctct ggaagttcga gactcccaag    660
tactatgtca ccgtcattgg taagccttgg tcgacacact agactcttat caacccgatc    720
```

```
tgtatcatta acgtgcatct tttagacgct cccggtcacc gtgatttcat caagaacatg    780
attactggta cttcccaggc tgactgcg                                        808

<210> SEQ ID NO 16
<211> LENGTH: 820
<212> TYPE: DNA
<213> ORGANISM: Epichloe amarillans

<400> SEQUENCE: 16
catcaacgtg gtcgttatcg taagttgact ttgacctgta tcattcgatg tatggataac     60
agttgctaac ttgtttgcta acaggggtac gtactgcgaa atatcactcg ccgttgccga    120
aattcacgta ctgactgaag cgtagccacg tcgactctgg caagtctacc accaccggtc    180
acttgatcta ccagtgcggt ggaattgaca agcgtaccat cgagaagttc gagaaggtaa    240
tatattctac tcctctcacg cataatatct gatgttcact cgttgcaatg cgagcctgcc    300
ttgtgtgtcg ctttgcaacc ttggtgggca agcaagcgac ttgcccgccc accaaagccc    360
ctctttttcg cccgcgatac gaatttttt tttttcggtc gcggggctca gtctgacttt     420
tggtggggca cctctcaacc cgtcactggt cttgggctag aagacgcaaa cgagagagac    480
atgacatgac attcgcgtgg ccccccaaaa aaaattgtga ttaaaaatca ctgacttgcc    540
ttcgctctat aggaagccgc cgaactcgga aagggttctt tcaaatatgc gtgggttctt    600
gacaagctca aggccgagcg tgagcgtggt atcaccatcg acattgccct ctggaagttc    660
gagactccca agtactatgt caccgtcatt ggtaagcctt ggtcgatgca ttagactctt    720
cttacccgat ctgcatcatt aacgtgcatc tattagacgc tcccggtcac cgtgatttca    780
tcaagaacat gattactggt acttcccagg ctgactgcgc                          820

<210> SEQ ID NO 17
<211> LENGTH: 520
<212> TYPE: DNA
<213> ORGANISM: Neotyphodium sp.

<400> SEQUENCE: 17
cgaggtcact cttggagaag ttgggcgttt tacggcagtg gccgcgccgc gctcccggtt     60
gcgaggtggt gtgttactac gcaaaggagg ctgcgacgag accgccgatt catttcaggg    120
gcggccgccg ccgcgaggcg ggcgagccgg tccccaacac caagcgcgca gcgggcttga    180
gggttgaaat gacgctcgaa caggcatgcc cgccagaata ctggcgggcg caatgtgcgt    240
tcaaagattc gatgattcac tgaattctgc aattcacatt acttatcgca tttcgctgcg    300
ttcttcatcg atgccagaac caagagatcc gttgttgaaa gttttgattc attcgatatt    360
caatccactc agacatgcgt aagaaaatac agaagggttt tggtccccg gcgggcgcct     420 agccccggcg ccccgcgag ggggcgtccg cggccgtgcc cgccgaggca acagtagagg      480
tataggtgca caggggtttg ggagtgtaaa ctcggtaatg                           520

<210> SEQ ID NO 18
<211> LENGTH: 513
<212> TYPE: DNA
<213> ORGANISM: Neotyphodium sp.

<400> SEQUENCE: 18
actcttggag aagttgggcg ttttacggca gtggccgcgc cgcgctcccg gttgcgaggt     60
ggtgtgttac tacgcaaagg aggctgcgac gagaccgccg attcatttca ggggcggccg    120
```

```
ccgccgcgag gcgggcgagc cggtccccaa caccaagcgc gcagcgggct tgagggttga      180
aatgacgctc gaacaggcat gcccgccaga atactggcgg gcgcaatgtg cgttcaaaga      240
ttcgatgatt cactgaattc tgcaattcac attacttatc gcatttcgct gcgttcttca      300
tcgatgccag aaccaagaga tccgttgttg aaagttttga ttcattcgat attcaatcca      360
ctcagacatg cgtaagaaaa tacagaaggg tttgggtccc ccggcgggcg cctagccccg      420
gcgcccccgc gaggggcgt ccgcggccgt gcccgccgag gcaacagtag aggtataggt       480
gcacaggggt tttgggagtg taaactcggt aat                                   513
```

```
<210> SEQ ID NO 19
<211> LENGTH: 516
<212> TYPE: DNA
<213> ORGANISM: Neotyphodium sp.

<400> SEQUENCE: 19
tcgaggtcac tcttggagaa gttgggcgtt tacggcagt ggccgcgccg cgctcccggt        60
tgcgaggtgg tgtgttacta cgcaaaggag gctgcgacga gaccgccgat tcatttcagg     120
ggcggccgcc gccgcgaggc gggcgagccg gtccccaaca ccaagcgcgc agcgggcttg     180
agggttgaaa tgacgctcga acaggcatgc ccgccagaat actggcgggc gcaatgtgcg     240
ttcaaagatt cgatgattca ctgaattctg caattcacat tacttatcgc atttcgctgc     300
gttcttcatc gatgccagaa ccaagagatc cgttgttgaa agttttgatt cattcgatat     360
tcaatccact cagacatgcg taagaaaata cagaagggtt ttggtccccc ggcgggcgcc     420
tagccccggc gccccgcga ggggcgtcc gcggccgtgc ccgccgaggc aacagtagag       480
gtataggtgc acaggggttt gggagtgtaa actcgg                               516
```

```
<210> SEQ ID NO 20
<211> LENGTH: 23
<212> TYPE: DNA
<213> ORGANISM: Artificial Sequence
<220> FEATURE:
<223> OTHER INFORMATION: Synthetic Primer

<400> SEQUENCE: 20
atgtccgtgg atggtgagca aac                                              23
```

```
<210> SEQ ID NO 21
<211> LENGTH: 23
<212> TYPE: DNA
<213> ORGANISM: Artificial Sequence
<220> FEATURE:
<223> OTHER INFORMATION: Synthetic Primer

<400> SEQUENCE: 21
atgcaatggg tgcctgtccg ttc                                              23
```

```
<210> SEQ ID NO 22
<211> LENGTH: 23
<212> TYPE: DNA
<213> ORGANISM: Artificial Sequence
<220> FEATURE:
<223> OTHER INFORMATION: Synthetic Primer

<400> SEQUENCE: 22
cgctgctctc tgtcatgcag aag                                              23
```

```
<210> SEQ ID NO 23
<211> LENGTH: 23
```

```
<212> TYPE: DNA
<213> ORGANISM: Artificial Sequence
<220> FEATURE:
<223> OTHER INFORMATION: Synthetic Primer

<400> SEQUENCE: 23
gttcctcatc caacatctcg atc                                              23

<210> SEQ ID NO 24
<211> LENGTH: 24
<212> TYPE: DNA
<213> ORGANISM: Artificial Sequence
<220> FEATURE:
<223> OTHER INFORMATION: Synthetic Primer

<400> SEQUENCE: 24
cgatcaccca actttacatg atac                                             24

<210> SEQ ID NO 25
<211> LENGTH: 24
<212> TYPE: DNA
<213> ORGANISM: Artificial Sequence
<220> FEATURE:
<223> OTHER INFORMATION: Synthetic Primer

<400> SEQUENCE: 25
acaagtcatg gtccggatgt gttg                                             24

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer

<400> SEQUENCE: 26
agatatggca tcgtgaccag cc                                               22

<210> SEQ ID NO 27
<211> LENGTH: 23
<212> TYPE: DNA
<213> ORGANISM: Artificial Sequence
<220> FEATURE:
<223> OTHER INFORMATION: Synthetic Primer

<400> SEQUENCE: 27
ggcatgtagc atcaaatggt gtc                                              23

<210> SEQ ID NO 28
<211> LENGTH: 22
<212> TYPE: DNA
<213> ORGANISM: Artificial Sequence
<220> FEATURE:
<223> OTHER INFORMATION: Synthetic Primer

<400> SEQUENCE: 28
atctaccaca agcttggcgg ac                                               22

<210> SEQ ID NO 29
<211> LENGTH: 22
<212> TYPE: DNA
<213> ORGANISM: Artificial Sequence
<220> FEATURE:
<223> OTHER INFORMATION: Synthetic Primer

<400> SEQUENCE: 29
```
gcggttgcat tgagaatcgc tc                                                    22

<210> SEQ ID NO 30
<211> LENGTH: 22
<212> TYPE: DNA
<213> ORGANISM: Artificial Sequence
<220> FEATURE:
<223> OTHER INFORMATION: Synthetic Primer

<400> SEQUENCE: 30
aagaaaggtg gacctgccat gg                                                    22

<210> SEQ ID NO 31
<211> LENGTH: 22
<212> TYPE: DNA
<213> ORGANISM: Artificial Sequence
<220> FEATURE:
<223> OTHER INFORMATION: Synthetic Primer

<400> SEQUENCE: 31
cttctcatcc gttaatgtgc gg                                                    22

<210> SEQ ID NO 32
<211> LENGTH: 22
<212> TYPE: DNA
<213> ORGANISM: Artificial Sequence
<220> FEATURE:
<223> OTHER INFORMATION: Synthetic Primer

<400> SEQUENCE: 32
gaacagtcgc ctgagtgacg ac                                                    22

<210> SEQ ID NO 33
<211> LENGTH: 22
<212> TYPE: DNA
<213> ORGANISM: Artificial Sequence
<220> FEATURE:
<223> OTHER INFORMATION: Synthetic Primer

<400> SEQUENCE: 33
gagatgtgct agacctgagt cg                                                    22

<210> SEQ ID NO 34
<211> LENGTH: 23
<212> TYPE: DNA
<213> ORGANISM: Artificial Sequence
<220> FEATURE:
<223> OTHER INFORMATION: Synthetic Primer

<400> SEQUENCE: 34
ggtctagtat tacgttgcca ggg                                                   23

<210> SEQ ID NO 35
<211> LENGTH: 22
<212> TYPE: DNA
<213> ORGANISM: Artificial Sequence
<220> FEATURE:
<223> OTHER INFORMATION: Synthetic Primer

<400> SEQUENCE: 35
gttgcccacg gtgcgcgtct tc                                                    22

<210> SEQ ID NO 36
<211> LENGTH: 25
<212> TYPE: DNA
<213> ORGANISM: Artificial Sequence

```
<220> FEATURE:
<223> OTHER INFORMATION: Synthetic Primer

<400> SEQUENCE: 36
gagacactag agaaatggca gctgc                                            25

<210> SEQ ID NO 37
<211> LENGTH: 24
<212> TYPE: DNA
<213> ORGANISM: Artificial Sequence
<220> FEATURE:
<223> OTHER INFORMATION: Synthetic Primer

<400> SEQUENCE: 37
ggcatccatg gtggcgaaga tgtg                                             24

<210> SEQ ID NO 38
<211> LENGTH: 23
<212> TYPE: DNA
<213> ORGANISM: Artificial Sequence
<220> FEATURE:
<223> OTHER INFORMATION: Synthetic Primer

<400> SEQUENCE: 38
ctctgatatg aagactcctg agc                                              23

<210> SEQ ID NO 39
<211> LENGTH: 23
<212> TYPE: DNA
<213> ORGANISM: Artificial Sequence
<220> FEATURE:
<223> OTHER INFORMATION: Synthetic Primer

<400> SEQUENCE: 39
gccaagcgga gttcagatca tcc                                              23

<210> SEQ ID NO 40
<211> LENGTH: 23
<212> TYPE: DNA
<213> ORGANISM: Artificial Sequence
<220> FEATURE:
<223> OTHER INFORMATION: Synthetic Primer

<400> SEQUENCE: 40
ctcgacgttt caacagattg cag                                              23

<210> SEQ ID NO 41
<211> LENGTH: 22
<212> TYPE: DNA
<213> ORGANISM: Artificial Sequence
<220> FEATURE:
<223> OTHER INFORMATION: Synthetic Primer

<400> SEQUENCE: 41
gtctttgaag acaagccagt cc                                               22

<210> SEQ ID NO 42
<211> LENGTH: 22
<212> TYPE: DNA
<213> ORGANISM: Artificial Sequence
<220> FEATURE:
<223> OTHER INFORMATION: Synthetic Primer

<400> SEQUENCE: 42
cgatggttgg atcagtcgtt gc                                               22
```

<210> SEQ ID NO 43
<211> LENGTH: 22
<212> TYPE: DNA
<213> ORGANISM: Artificial Sequence
<220> FEATURE:
<223> OTHER INFORMATION: Synthetic Primer

<400> SEQUENCE: 43
gagctgatgc ggcattggca tc                                        22

<210> SEQ ID NO 44
<211> LENGTH: 23
<212> TYPE: DNA
<213> ORGANISM: Artificial Sequence
<220> FEATURE:
<223> OTHER INFORMATION: Synthetic Primer

<400> SEQUENCE: 44
cactgacctc caagtatact tgc                                       23

<210> SEQ ID NO 45
<211> LENGTH: 23
<212> TYPE: DNA
<213> ORGANISM: Artificial Sequence
<220> FEATURE:
<223> OTHER INFORMATION: Synthetic Primer

<400> SEQUENCE: 45
cgtcatcccg acctctttcg gat                                       23

<210> SEQ ID NO 46
<211> LENGTH: 23
<212> TYPE: DNA
<213> ORGANISM: Artificial Sequence
<220> FEATURE:
<223> OTHER INFORMATION: Synthetic Primer

<400> SEQUENCE: 46
accaagccaa cggatatctt cgc                                       23

<210> SEQ ID NO 47
<211> LENGTH: 23
<212> TYPE: DNA
<213> ORGANISM: Artificial Sequence
<220> FEATURE:
<223> OTHER INFORMATION: Synthetic Primer

<400> SEQUENCE: 47
acgtctttgg tccgtcttgt tag                                       23

<210> SEQ ID NO 48
<211> LENGTH: 22
<212> TYPE: DNA
<213> ORGANISM: Artificial Sequence
<220> FEATURE:
<223> OTHER INFORMATION: Synthetic Primer

<400> SEQUENCE: 48
gttctaaaca tcgtgactgg gc                                        22

<210> SEQ ID NO 49
<211> LENGTH: 23
<212> TYPE: DNA
<213> ORGANISM: Artificial Sequence
<220> FEATURE:
<223> OTHER INFORMATION: Synthetic Primer

<400> SEQUENCE: 49
ggtaggtcag catcttgtca acg                                          23

<210> SEQ ID NO 50
<211> LENGTH: 23
<212> TYPE: DNA
<213> ORGANISM: Artificial Sequence
<220> FEATURE:
<223> OTHER INFORMATION: Synthetic Primer

<400> SEQUENCE: 50
gtgaactggc agtagtccgt atg                                          23

<210> SEQ ID NO 51
<211> LENGTH: 23
<212> TYPE: DNA
<213> ORGANISM: Artificial Sequence
<220> FEATURE:
<223> OTHER INFORMATION: Synthetic Primer

<400> SEQUENCE: 51
aatccatgcc agtgtcggga atg                                          23

<210> SEQ ID NO 52
<211> LENGTH: 23
<212> TYPE: DNA
<213> ORGANISM: Artificial Sequence
<220> FEATURE:
<223> OTHER INFORMATION: Synthetic Primer

<400> SEQUENCE: 52
catccatgac gtgccaaaca atc                                          23

<210> SEQ ID NO 53
<211> LENGTH: 21
<212> TYPE: DNA
<213> ORGANISM: Artificial Sequence
<220> FEATURE:
<223> OTHER INFORMATION: Synthetic Primer

<400> SEQUENCE: 53
tcgcagctgc aagtcgagca c                                            21

<210> SEQ ID NO 54
<211> LENGTH: 23
<212> TYPE: DNA
<213> ORGANISM: Artificial Sequence
<220> FEATURE:
<223> OTHER INFORMATION: Synthetic Primer

<400> SEQUENCE: 54
cgtcgtggta acgcacgcaa acg                                          23

<210> SEQ ID NO 55
<211> LENGTH: 23
<212> TYPE: DNA
<213> ORGANISM: Artificial Sequence
<220> FEATURE:
<223> OTHER INFORMATION: Synthetic Primer

<400> SEQUENCE: 55
cagtctgcct tgccgaccgg ggt                                          23

<210> SEQ ID NO 56

```
<211> LENGTH: 22
<212> TYPE: DNA
<213> ORGANISM: Artificial Sequence
<220> FEATURE:
<223> OTHER INFORMATION: Synthetic Primer

<400> SEQUENCE: 56
cgacgactgg ctgtggagga tg                                              22

<210> SEQ ID NO 57
<211> LENGTH: 23
<212> TYPE: DNA
<213> ORGANISM: Artificial Sequence
<220> FEATURE:
<223> OTHER INFORMATION: Synthetic Primer

<400> SEQUENCE: 57
ctagcctcca gatcttgtga aag                                             23

<210> SEQ ID NO 58
<211> LENGTH: 23
<212> TYPE: DNA
<213> ORGANISM: Artificial Sequence
<220> FEATURE:
<223> OTHER INFORMATION: Synthetic primer

<400> SEQUENCE: 58
gcacaaacaa taaattcggc caa                                             23

<210> SEQ ID NO 59
<211> LENGTH: 23
<212> TYPE: DNA
<213> ORGANISM: Artificial Sequence
<220> FEATURE:
<223> OTHER INFORMATION: Synthetic Primer

<400> SEQUENCE: 59
aatttgccct ctgttaaatc ctc                                             23

<210> SEQ ID NO 60
<211> LENGTH: 23
<212> TYPE: DNA
<213> ORGANISM: Artificial Sequence
<220> FEATURE:
<223> OTHER INFORMATION: Synthetic Primer

<400> SEQUENCE: 60
gtgatcggtg ctgacggggt cca                                             23

<210> SEQ ID NO 61
<211> LENGTH: 24
<212> TYPE: DNA
<213> ORGANISM: Artificial Sequence
<220> FEATURE:
<223> OTHER INFORMATION: Synthetic Primer

<400> SEQUENCE: 61
tatcgccata tttgctcctt gccc                                            24

<210> SEQ ID NO 62
<211> LENGTH: 23
<212> TYPE: DNA
<213> ORGANISM: Artificial Sequence
<220> FEATURE:
<223> OTHER INFORMATION: Synthetic Primer

<400> SEQUENCE: 62
```

```
atattgaatt gctgcgtgag gag                                              23

<210> SEQ ID NO 63
<211> LENGTH: 24
<212> TYPE: DNA
<213> ORGANISM: Artificial Sequence
<220> FEATURE:
<223> OTHER INFORMATION: Synthetic Primer

<400> SEQUENCE: 63
agaggccaag aagcggcctg gaca                                             24

<210> SEQ ID NO 64
<211> LENGTH: 23
<212> TYPE: DNA
<213> ORGANISM: Artificial Sequence
<220> FEATURE:
<223> OTHER INFORMATION: Synthetic Primer

<400> SEQUENCE: 64
aacatcgcct gggagctcgt ata                                              23

<210> SEQ ID NO 65
<211> LENGTH: 21
<212> TYPE: DNA
<213> ORGANISM: Artificial Sequence
<220> FEATURE:
<223> OTHER INFORMATION: Synthetic Primer

<400> SEQUENCE: 65
cgcaggtcct atttccatcg c                                                21

<210> SEQ ID NO 66
<211> LENGTH: 20
<212> TYPE: DNA
<213> ORGANISM: Artificial Sequence
<220> FEATURE:
<223> OTHER INFORMATION: Synthetic Primer

<400> SEQUENCE: 66
gaaactgcca atcgagcata                                                  20

<210> SEQ ID NO 67
<211> LENGTH: 23
<212> TYPE: DNA
<213> ORGANISM: Artificial Sequence
<220> FEATURE:
<223> OTHER INFORMATION: Synthetic Primer

<400> SEQUENCE: 67
ttcttgcaat cattttgcaa ttg                                              23

<210> SEQ ID NO 68
<211> LENGTH: 20
<212> TYPE: DNA
<213> ORGANISM: Artificial Sequence
<220> FEATURE:
<223> OTHER INFORMATION: Synthetic Primer

<400> SEQUENCE: 68
gaattatgtt actcttgggg                                                  20

<210> SEQ ID NO 69
<211> LENGTH: 20
<212> TYPE: DNA
```

```
<213> ORGANISM: Artificial Sequence
<220> FEATURE:
<223> OTHER INFORMATION: Synthetic Primer

<400> SEQUENCE: 69
aagttggcac ataggtcttc                                               20

<210> SEQ ID NO 70
<211> LENGTH: 23
<212> TYPE: DNA
<213> ORGANISM: Artificial Sequence
<220> FEATURE:
<223> OTHER INFORMATION: Synthetic Primer

<400> SEQUENCE: 70
ctaccaggac aggcgtgacg tcc                                           23

<210> SEQ ID NO 71
<211> LENGTH: 23
<212> TYPE: DNA
<213> ORGANISM: Artificial Sequence
<220> FEATURE:
<223> OTHER INFORMATION: Synthetic Primer

<400> SEQUENCE: 71
cagaggttta accctcttga cgc                                           23

<210> SEQ ID NO 72
<211> LENGTH: 27
<212> TYPE: DNA
<213> ORGANISM: Artificial Sequence
<220> FEATURE:
<223> OTHER INFORMATION: Synthetic Primer

<400> SEQUENCE: 72
atggctgtca ttcatacaac agctatg                                       27

<210> SEQ ID NO 73
<211> LENGTH: 26
<212> TYPE: DNA
<213> ORGANISM: Artificial Sequence
<220> FEATURE:
<223> OTHER INFORMATION: Synthetic Primer

<400> SEQUENCE: 73
agcgtcccgg acaggcatat ctccca                                        26

<210> SEQ ID NO 74
<211> LENGTH: 20
<212> TYPE: DNA
<213> ORGANISM: Artificial Sequence
<220> FEATURE:
<223> OTHER INFORMATION: Synthetic Primer

<400> SEQUENCE: 74
ccaagcatcg atttgtcacc                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic Primer

<400> SEQUENCE: 75
aatctgatcg ccatctttgc                                               20
```

```
<210> SEQ ID NO 76
<211> LENGTH: 20
<212> TYPE: DNA
<213> ORGANISM: Artificial Sequence
<220> FEATURE:
<223> OTHER INFORMATION: Synthetic Primer

<400> SEQUENCE: 76
ccgagtttga tgacctgctg                                                   20

<210> SEQ ID NO 77
<211> LENGTH: 20
<212> TYPE: DNA
<213> ORGANISM: Artificial Sequence
<220> FEATURE:
<223> OTHER INFORMATION: Synthetic Primer

<400> SEQUENCE: 77
ttccgcttcc gagtagactc                                                   20
```

FUNGAL ENDOPHYTES OF *ELYMUS CANADENSIS*

This application claims the priority of U.S. provisional application Ser. No. 60/889,480, filed Feb. 12, 2007, the entire disclosure of which is incorporated herein by reference.

BACKGROUND OF THE INVENTION

1. Field of the Invention

This invention relates to fungal endophytes of host plants, such as the grass *Elymus canadensis* (Canada wild rye—CWR). In particular the invention relates to epichloë endophytes (i.e. *Neotyphodium*) which do not interfere with flowering by their host plants, and to synthetic combinations of these endophytes with improved strains of a host plant.

2. Description of the Related Art

*Elymus canadensis* (Canada wild rye—"CWR") is a native perennial cool season bunch grass, a member of the Triticeae host tribe that is known to harbor clavicipitaceous fungal endophytes (Bultman & White, 1988; White & Bultman, 1987; Schardl & Leuchtmann, 1999; Vinton et al., 2001). It is tolerant to a range of soils, winter hardy, and able to grow across the United Sates and as far north as southern Alaska. Canada wild rye is often used for prairie restoration, conservation and erosion stabilization, and young CWR plant tissue is palatable and nutritious to grazing animals. In particular, CWR has been reported to harbor an ascomycete fungal endophyte, *Epichloë elymi*. The fungal endophyte systemically colonizes intercellular spaces of leaf blades, leaf sheaths and culms of the host plant, and is typically seed transmissible, although infection of other plant parts may also occur. Endophytic fungi are often considered to be involved in a symbiotic relationship with their host plant, and such fungi have been utilized in grass breeding research programs (Bouton et al., 2002).

Previous studies have indicated that epichloë endophytes identified in *Elymus* species are *Epichloe elymi*, which are of sexual origin and have the ability to form stroma and perithecia on the plant culm and interfere with development ("choke") the developing inflorescence (Bultman & White, 1988; White & Bultman, 1987; Schardl & Leuchtmann, 1999), resulting in reduced growth and reproduction of the host plant. In one study of endophyte-infected CWR prairie grasses, formation of sexual reproductive structures (stroma, perithecia, and/or ascospores) by an endophyte did not occur. However, the endophytes from that study were not subjected to phylogenetic analysis (Vinton et al. 2001). *Epichloë* and *Neotyphodium* species and strains are thought to have arisen and co-evolved with host plant species, and hybridization events between endophytes, resulting in formation of new endophytic strains and species, displaying either or both of sexual and asexual reproductive forms, is also thought to have occurred. *Hordeum bogdanii* was recently shown to contain an endophyte that apparently arose via such a hybridization event (Moon et al., 2004).

Many epichloë endophytes provide bioprotection to their hosts by producing alkaloids and other metabolites that have anti-insect and anti-herbivore properties. More recently, the genes required for the biosynthesis of some of these compounds, known as peramine, lolines, indole-diterpenes and ergot alkaloids have been isolated and sequenced (Damrongkool et al., 2005; Spiering et al., 2005; Tanaka et al., 2005; Wang et al., 2004; Young et al. 2006). *E. elymi* is known to produce the insect feeding deterrent peramine (Clay & Schardl, 2002; Schardl & Leuchtmann, 1999; Siegel et al., 1990), while *Epichloë amarillans*, an endophyte of the Aveneae host tribe may also produce alkaloids such as lolines. Thus CWR plants colonized by endophytes, including *Epichloë* sp. and *Neotyphodium* strains, may be tested for the presence of fungal metabolites.

U.S. Pat. No. 6,111,170 describes synthetic combinations of endophyte/fescue cultivars. U.S. Patent Publications 20060121593 and 20060150273 relate to grass endophytes, such as *Neotyphodium lolii* and *Neotyphodium coenophialum*.

While it is known in the art that the presence of a fungal endophyte can lead to enhanced vegetative growth of a host plant, the endophyte may reduce the host plant's reproductive fitness by interfering with flower development, or may reduce the agronomic value of a host plant crop by production of toxic metabolites such as alkaloids. Thus, there is a need in the art to improve the agronomic properties of host forage grasses such as *E. canadensis*, as well as to promote the seed yield of a host plant, by protecting the grass from *Epichloë* sp. that produce metabolites at levels toxic to herbivores and/or that reproduce sexually.

SUMMARY OF THE INVENTION

In one aspect, the invention provides an isolated *Neotyphodium* sp. endophyte selected from the group consisting of: NFE1000, NFE1001, and NFE1002, cultures of the endophyte having been deposited with NRRL accession numbers NRRL 50005, NRRL 50004, and NRRL 50003, respectively. In another aspect, the invention provides a synthetic combination of the endophyte and a host plant.

In one embodiment, the *Neotyphodium* sp. endophyte is in combination with a host grass plant, cultures of the endophyte having been deposited with NRRL accession numbers NRRL 50005, NRRL 50004, and NRRL 50003, respectively, such that the host grass plant displays at least equivalent reproductive vigor as a host grass plant identical except for the absence of the endophyte when compared under identical conditions, the endophyte protects the host grass from at least one pest and/or abiotic stress, and the host grass or a parental generation of the host grass is artificially inoculated with the endophyte. In certain embodiments, the endophyte-host combination comprises a combination wherein the host grass plant is a member of the Aveneae or Triticeae tribes. In a particular embodiment, the host plant is an *Elymus canadensis* host plant.

The combination may be achieved by introduction of the endophyte to the host grass by a method selected from the group consisting of: inoculation, infection, grafting, and seed transmission. In certain embodiments, the endophyte-host plant combination may exhibit resistance or tolerance to an abiotic stress selected from the group consisting of: water deficiency, nutrient deficiency, heat stress, salt toxicity, aluminum toxicity, and freezing temperatures. In other embodiments, the endophyte-host plant combination may exhibit resistance or tolerance to a biotic stress selected from the group consisting of: insect infestation, nematode infestation, and herbivore grazing. Seed of a host grass plant-endophyte combination comprising the endophyte is another embodiment of the invention.

In another aspect, the invention relates to a method for propagating an *Elymus canadensis-Neotyphodium* sp. combination, comprising: a) producing seed, comprising an *Elymus canadensis-Neotyphodium* sp. combination, by a method comprising: i) obtaining an *Elymus canadensis* host grass plant in combination with *Neotyphodium* sp., the *Neotyphodium* sp. having been deposited with NRRL accession numbers NRRL 50005, NRRL 50004, or NRRL 50003, respectively, and ii) harvesting seed comprising the combination from the plant; the plant or a parental generation of the plant having been inoculated with *Neotyphodium* sp. endophyte, or the *Neotyphodium* sp. having been introduced into a parental generation of the plant through crossing and/or backcrossing procedures, and cultures of the endophyte having been deposited with NRRL accession numbers NRRL 50005, NRRL 50004, and NRRL 50003; or b) vegetatively reproducing *Elymus canadensis* plant tissue colonized by a *Neotyphodium* sp. NFE1000, NFE1001, or NFE1002, cultures of the *Neotyphodium* sp. having been deposited with NRRL accession numbers NRRL 50005, NRRL 50004, and NRRL 50003, respectively.

The invention further relates to a method for enhancing the growth or reproduction of an *Elymus canadensis* host grass plant in the presence of a biotic or abiotic stress, comprising: contacting the host grass plant with a strain of endophyte of *Neotyphodium* sp., cultures of the endophyte having been deposited with NRRL accession numbers: NRRL 50005, NRRL 50004, and NRRL 50003, such that the endophyte colonizes the plant. The host grass plant may have enhanced root growth, more tillers, enhanced total biomass, or enhanced seed yield in comparison to an otherwise identical host grass plant lacking the endophyte. The stress may be selected from the group consisting of: a biotic stress, a pest stress, an insect stress, an abiotic stress, and a water deficit stress. The stress may be a biotic stress caused by at least one organism selected from the group consisting of an herbivore, a nematode, and an insect. Alternatively, the stress may be an abiotic stress. The insect, to which increased resistance may be conferred on the host grass, is selected from the group consisting of: fall armyworm and Russian wheat aphid. Colonization of the host grass may be achieved by introduction of the endophyte to the host grass by a method selected from the group consisting of: inoculation, infection, grafting, seed transmission, and combinations thereof.

In another aspect, the invention provides a method for detecting the presence of a *Neotyphodium* sp. endophyte, cultures of the endophyte having been deposited with NRRL accession numbers NRRL 50005, NRRL 50004, and NRRL 50003, comprising: a) isolating DNA from tissues of a host grass plant comprising the DNA of a *Neotyphodium* sp. endophyte, cultures of the endophyte having been deposited with NRRL accession numbers: NRRL 50005, NRRL 50004, and NRRL 50003; b) analyzing the DNA and c) detecting the presence of DNA derived from an endophyte *Neotyphodium* sp., cultures of the endophyte having been deposited with NRRL accession numbers: NRRL 50005, NRRL 50004, and NRRL 50003. In certain embodiments, the host grass plant is *Elymus canadensis*.

The invention further provides an isolated nucleic acid sequence selected from the group consisting of SEQ ID NO:2, SEQ ID NO:3, SEQ ID NO:4, SEQ ID NO:5, SEQ ID NO:6, and SEQ ID NO:7.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 2. Representative alignment of tub2 sequence from GenBank Accession AY137610 (SEQ ID NO:8) with tub2 sequences from strains NFE1000, NFE1001, and NFE1002, copies 1 and 2 (SEQ ID NOs:9-11).

DETAILED DESCRIPTION OF THE INVENTION

Figure 1:
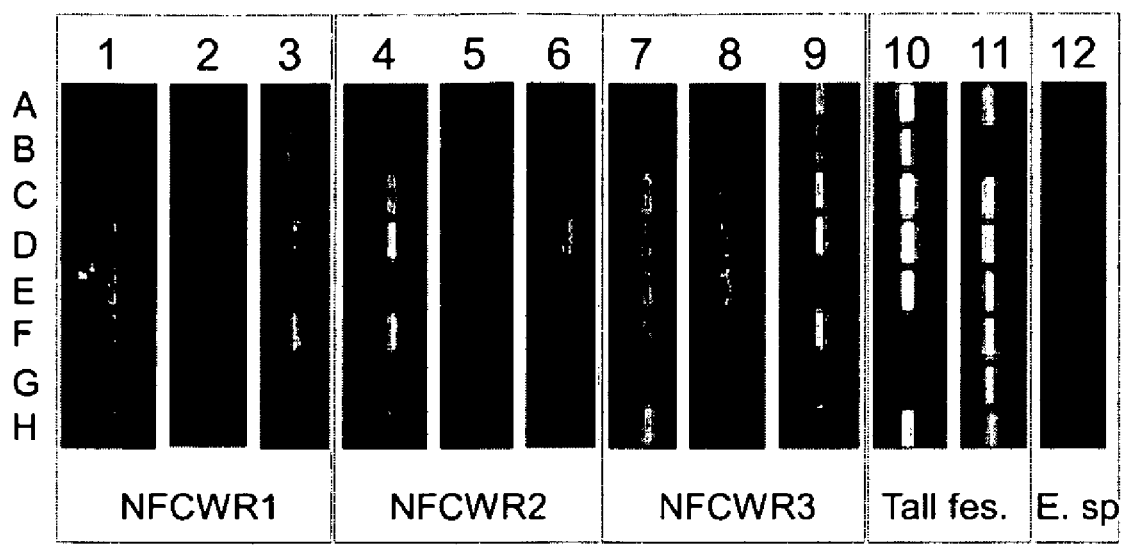
FIG. 1. High throughput analysis of grasses for endophyte infection. A PCR screen for endophyte detection in CWR plants. PCR was performed with the Tef primers (SEQ ID NOs:2-3). The samples have been arranged to represent the format (96 well plate) of DNA isolation. Columns 1-3 contain samples infected with NFE1000; 4-6 with NFE1001; 7-9 with NFE1002; 10-11 endophyte-infected tall fescue; 12 *Elymus* species: A12, *E. pendulinus*; B12, *E. nevskii*; C12, *E. breviaristatus*; D12, *E. sibiricus*; E12, *E. mutabilis*; F12, *E. lanceolatus*; G12, *E. trachycaulus*; H12, *E. wawawaiensis*.

The invention provides isolated clavicipitaceous fungal endophytes from endophyte-infected accessions of *Elymus canadensis* (CWR), these endophytes having been characterized taxonomically and with respect to their production of potentially toxic alkaloids. These endophytes may be classified as asexually reproducing *Neotyphodium* strains. In particular embodiments the *Neotyphodium* (formerly *Acremonium*) fungal endophyte may be of a strain selected from the group consisting of: NFE1000, NFE1001, and NFE1002, cultures of the endophyte having been deposited with NRRL (USDA Agricultural Research Service Culture Collection, 1815 N. University Street, Peoria, Ill. 61604), under accession numbers NRRL 50005, NRRL 50004, and NRRL 50003, respectively.

In another aspect, the invention further provides a combination (also termed a "symbiotum") of a host plant and a *Neotyphodium* endophyte that allows for improved agronomic properties of the CWR host plants. In a particular embodiment, the host plant is *E. canadensis* (CWR). The combination may be achieved by artificial inoculation, application, or other infection of a host plant, such as CWR, or host plant tissues with a *Neotyphodium* strain of the present invention. Thus a combination achieved by such an inoculation is termed a "synthetic" combination. The fungal endophyte may be present in intercellular spaces within plant tissue. Its presence may also occur or may also be maintained within a CWR plant or plant population by means of seed transmission, grafting or other inoculation method, or crossing/backcrossing procedures. These endophytes may also be introduced or maintained by such procedures, into various Triticeae grasses, such as barley (*Hordeum vulgare*), wheat (*Triticum aestivum*), durum wheat (*Triticum turgidum* ssp. durum), tall wheatgrass (*Thinopyrum ponticum*), western wheatgrass (*Pascopyrum smithii*), cereal rye (*Secale cereale*), and Russian wild rye (*Psathyrostachys juncea*). These endophytes may also be introduced into *Aveneae* grasses, such as oats (*Avena sativa*) and creeping bentgrass (*Agrostis stolonifera*).

In certain embodiments, the agronomic qualities may be selected from the group consisting of: increased biomass, increased tillering, increased root mass, increased flowering, increased seed yield, and enhanced resistance to biotic and/or abiotic stresses, each of these qualities being rated in comparison to otherwise identical plants grown under the same conditions, and differing only with respect to the presence or absence of a fungal endophyte. The stresses may include, for instance, drought (water deficit), cold, heat stress, nutrient deficiency, salt toxicity, aluminum toxicity, grazing by herbivores, insect infestation, nematode infection, and fungal infection, among others. In a particular embodiment, the enhanced resistance to fungal infection protects the host plant from subsequent infection by *Epichloë* sp., allowing for improved seed yield relative, for instance, to CWR plants colonized by sexually reproducing strains of *Epichloë* sp. In another embodiment, the invention may be defined as a CWR seed in combination with a *Neotyphodium* strain of the present invention. In yet another embodiment, the insect infestation is caused by Russian wheat aphid (*Diuraphis noxia*), or fall armyworm (*Spodoptera frugiperda*). The endophyte may also confer resistance to various nematode species, including *Pratylenchus* spp. and root knot nematode (*Meloidogyne* spp.; *Meloidogyne marylandi*).

The invention also relates to methods for protecting *E. elymus* plants from biotic or abiotic stress, by means of introducing a *Neotyphodium* strain of the present invention into a CWR plant, and propagating the plant-endophyte combination. Such propagation (of the plant) may be vegetative or by sexual means. Vegetative propagation of the plant allows for propagation of the combination since fungal propagules (e.g. mycelia, conidia, and ascospores) are present in or on plant tissue or may infect the plant tissue. In another embodiment, the combination may also be propagated by seed production of the plant along with seed transmission of the endophyte.

Yet another embodiment of the invention relates to methods for detecting the presence of *Neotyphodium* strain of the present invention within a host plant, such as CWR. This may be accomplished, for instance, by isolation of total DNA from tissues of a potential plant-endophyte combination, followed by PCR, or alternatively, Southern blotting or other method known in the art, to detect the presence of specific sequences associated with the presence of a *Neotyphodium* strain of the present invention. In particular embodiments, nucleotide primers comprising sequences of SEQ ID NO:2—SEQ ID NO:7 may be utilized in a PCR-based assay to detect such a combination.

Alternatively, biochemical methods such as ELISA, HPLC, TLC, or fungal metabolite assays may be utilized to determine the presence of a *Neotyphodium* strain of the present invention in a given sample of CWR tissue. In particular embodiments, a potential CWR-endophyte combination may be assayed to determine whether any of peramine, ergot alkaloids, lolitrems (indole-diterpenes), or lolines are present.

As described below, CWR accessions were collected from Texas (NFCWR1 and NFCWR3), and Mexico (NFCWR2). These *Elymus* species were determined to be endophyte-infected but stroma did not form during cultivation of the grass plant. The endophytes present in the NFCWR accessions were characterized based on their phylogenetic origin and toxin synthesis potential. The identification and toxin (e.g. alkaloid) content characterization of asexual endophytes present in CWR can enable utilization of these endophytes within a CWR breeding program to create CWR plants with improved agronomic qualities and seed yields due to the presence of the fungal endophyte.

In addition to inoculation of a particular plant genotype with an endophytic *Neotyphodium* strain prepared according to the current invention, a CWR-*Neotyphodium* combination may be prepared, for instance in a breeding program, by crossing two CWR plants, or a CWR plant with another species, followed by backcrossing procedures, wherein the maternal plant parent is in combination with a *Neotyphodium* strain of the present invention, to produce hybrid seed also comprising fungal tissue. Therefore, the current invention not only encompasses a plant comprising an endophytic strain in accordance with the current invention, but also the progeny of such a plant or plants. As used herein the term "progeny" denotes the offspring of any generation of a parent plant prepared in accordance with the instant invention, wherein the progeny comprises an endophytic fungal strain of the present invention.

Deposit Information

A deposit of *Neotyphodium* sp. NFE1000, NFE1001, and NFE1002, disclosed above and recited in the claims, has been made with the NRRL culture collection (USDA NRRL Agricultural Research Service Culture Collection, 1815 N. University St., Peoria, Ill. 61604). The date of deposit was Feb. 8, 2007. Upon issuance of a patent, all restrictions upon the deposit will be removed, and the deposit is intended to meet all of the requirements of 37 C.F.R. §1.801-1.809. The accession numbers for those deposited cultures are NRRL Accession Nos. NRRL 50005, NRRL 50004, and NRRL 50003, for strains NFE1000, NFE1001, and NFE1002, respectively. The deposit will be maintained in the depository for a period of 30 years, or 5 years after the last request, or for the effective life of the patent, whichever is longer, and will be replaced if necessary during that period.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Endophyte Isolation and Culture, Isolation of Fungal DNA, and PCR and Sequence Analysis A. Endophyte Isolation and Culture Three CWR accessions were collected from Texas (NFCWR1 and NFCWR3), and Mexico (NFCWR2). These Elymus accessions were determined to be endophyte-infected but stroma did not form during cultivation. Two additional CWR accessions from Oklahoma, also infected by *Epichloë elymi*, were included in the comparison. The additional *Epichloë elymi* isolates from these accessions were capable of producing stroma on host plant tissues. Fungal isolates (Table 1) were isolated directly from endophyte-infected pseudostems (Moon et al., 2002). Cultures were maintained on Potato dextrose (PD) agar at 22° C.

Seventy two plants from three NFCWR accessions were screened for endophyte infection. Since the narrow stems of the CWR plants were not suitable for analysis with an endophyte specific immunoblot, the plants were screened for endophyte infection using aniline blue staining of leaf peels (Clark et al., 1983) and PCR with primers specific to epichloë endophytes. The fragile nature of the CWR stems made leaf peels very labor intensive and difficult to obtain consistent results. However, PCR was successful in detecting the presence of epichloë specific sequences from total DNA extracted from the base of CWR pseudostems (FIG. 1). PCR of the three CWR accessions indicated endophyte infection rates of 83%, 21% and 96% (FIG. 1). Other *Elymus* species and tall fescue were screened for endophyte infection which indicated 0% and 88% infection respectively (FIG. 1). Seed storage prior to germination may have resulted in the loss of endophyte infection of the other *Elymus* species.

The endophytes NFE1000, NFE1001 and NFE1002 (Table 1), were isolated from the NFCWR stems and maintained in culture on PD agar. NFE culture morphology was typically white and cottony; the isolates did not produce conidia on PD agar. Two sexually reproducing epichloë endophytes were also isolated from stroma present on choked CWR plants from Oklahoma, USA. Comparison of the amplified ITS sequence from these isolated cultures with an available ITS sequence (GenBank Accession DQ899096; SEQ ID NO:1) revealed that these cultures were *E. elymi*, a sexually reproducing isolate known to be present in *Elymus canadensis*. The *E. elymi* culture morphology is white and cottony and grows faster than the NFE isolates.

TABLE 1

Biological cultures

| Strain name | Species | Host plant | Location |
|---|---|---|---|
| NFE1000 | EcaTG-1 | *Elymus canadensis*[1] | Texas |
| NFE1001 | EcaTG-1 | *E. canadensis*[1] | Mexico |
| NFE1002 | EcaTG-1 | *E. canadensis*[1] | Texas |
| EC1 | *Epichloë elymi* | *E. canadensis* | Oklahoma |
| EC4 | *E. elymi* | *E. canadensis* | Oklahoma |

[1]NFCWR plants

B. Isolation of Fungal DNA, PCR, and Sequence Analysis

Genomic DNA was isolated from ~0.5 mm of tissue from the base of individual plant pseudostems of unknown endophyte status. The samples were placed in a 1.2 mL collection tube in 96 well format containing a 5 mm steel BB and freeze-dried overnight. The samples were then ground in liquid nitrogen using a TissueLyser (Qiagen, Valencia, Calif.). The genomic DNA was extracted using the MagAttract® 96 DNA plant core kit (Qiagen) as per the manufacturer's instructions. Genomic DNA from pure endophyte cultures was isolated using the DNeasy® Plant mini kit (Qiagen) according to the manufacturer's instructions.

PCR was used to detect endophyte genomic DNA sequences within total DNA extracted from grass samples. The PCR reaction was based on primers that anneal to the endophyte translation elongation factor 1-α (tef1), tef1-exon1d-1, and tef1-exon4u-1 (Craven et al., 2001):

tef1-exon1d-1: GGGTAAGGACGAAAAGACTCA; (SEQ ID NO:2)

tef1-exon4u-1: CGGCAGCGATAATCAGGATAG; (SEQ ID NO:3), respectively.

Phylogenetic analysis was performed using primers designed to tef1, and to the ribosomal internal transcribed spacer (ITS) region (White et al., 1996) and tubulin tub2 gene (Craven et al., 2001; Moon et al., 2004), also using additional primers:

ITS4:
TCCTCCGCTTATTGATATGC, (SEQ ID NO:4)

ITS5:
GGAAGTAAAAGTCGTAACAAGG, (SEQ ID NO:5)

T1.1:
GAGAAAATGCGTGAGATTGT, (SEQ ID NO:6)
and

T1.2:
CTGGTCAACCAGCTCAGCAC. (SEQ ID NO:7)

PCR reactions were performed in 25 or 50 µL reaction volumes containing 5-100 ng of DNA, 1× green reaction buffer (Promega, Madison, Wis.); 200 µM each dNTPs; 200 nM of each primer; and 1 U GoTaq® (Promega). The PCR cycle was as follows: 94° C. for 2 minutes; 30 cycles of 94° C. for 15 seconds and 58° C. for 30 seconds; and 72° C. for 1 minute. The PCR products were separated on 2% agarose in 1×TBE (Invitrogen, Carlsbad, Calif.), stained with ethidium bromide and visualized under UV light.

PCR products were cloned directly into pGEM®-T-easy (Promega) and used to transform *E. coli* XL1 blue cells. Plasmid DNA was isolated from twelve independent colonies per amplified gene using QIAprep spin miniprep kit (Qiagen) and sequenced. PCR fragments were directly sequenced after purification with the QIAquick PCR purification kit (Qiagen). The sequence data were edited using Sequencher™ 4.6 (Gene Codes, Ann Arbor, Mich.).

Example 2

Phylogenetic Analysis

Phylogenetic analysis was performed as per Craven et al., 2001 using maximum parsimony that utilized the branch and bound search in PAUP (Swofford, 1998). PCR and sequence analysis of amplified endophyte DNA fragments of strains NFE1000-NFE1002 (SEQ ID NOs:17-19, respectively) corresponding to the ITS region (GenBank accession DQ899096; SEQ ID NO:1) combined with phylogenetic analysis revealed that the NFE isolates were more similar to *E. amarillans* than *E. elymi*. While the ITS sequence analysis was informative, only one progenitor copy is maintained after interspecific hybridization (Ganley & Scott, 2002) and therefore ITS phylogenetic analysis was used in combination with additional analysis. Thus, additionally, amplified tub2 and tef1 PCR bands from the NFE isolates (e.g. Example 1) were cloned into pGEM-T-easy® to sequence individual fragments. Analysis of the tub2 and tef1 sequences from the NFE isolates demonstrated that two distinct copies were present in each fungal isolate.

Figure 2:
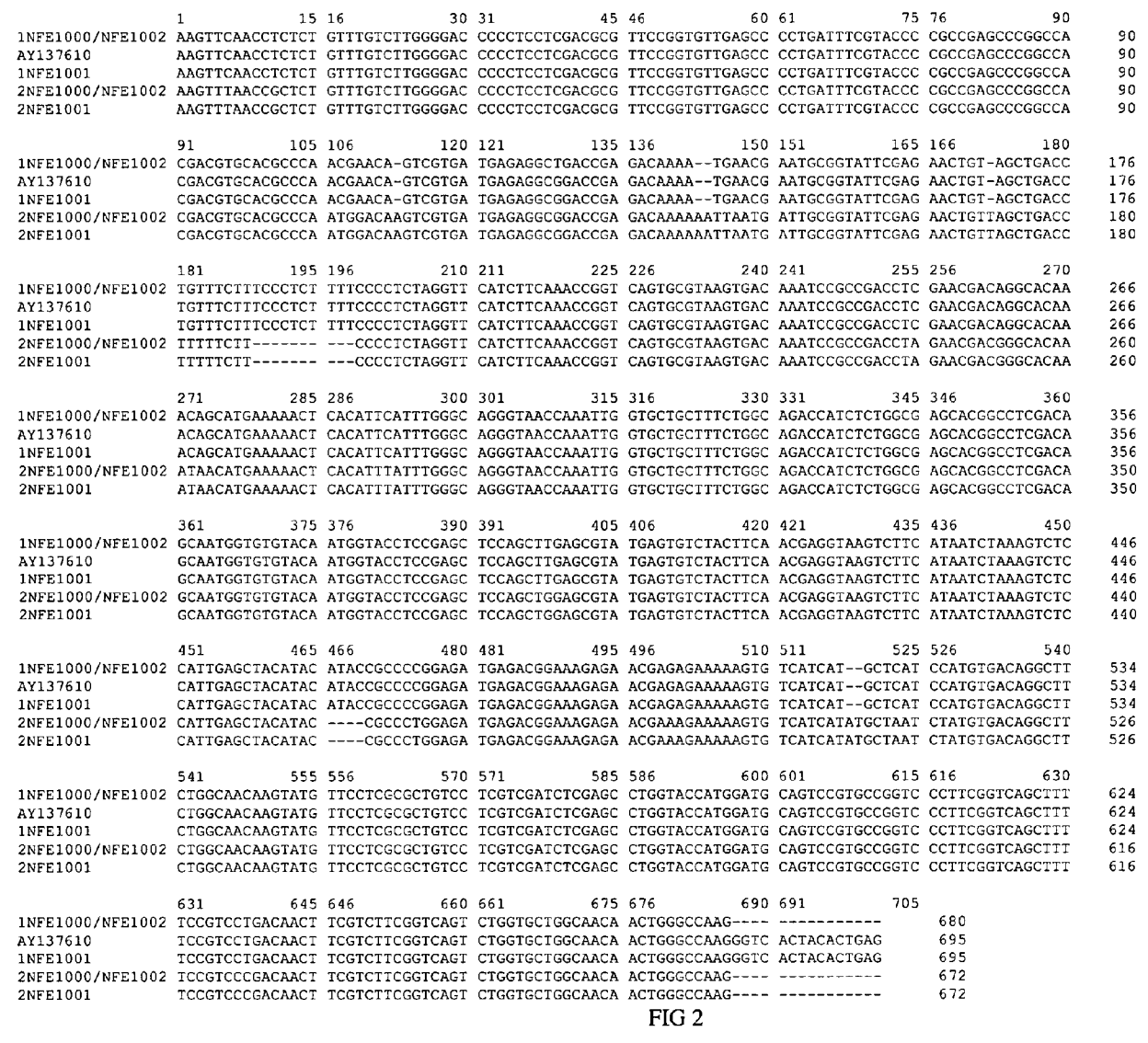

Analysis also showed that one copy ("copy 1") of the amplified tub2 sequence (SEQ ID NO:9) was identical in each of isolates NFE1000 and NFE1002, and differed from the amplified tub2 sequence of NFE1001 (SEQ ID NO:11) and from the copy 1 beta tubulin (tub2) gene of GenBank accession AY137610 (SEQ ID NO:8). The second copy ("copy 2") of the amplified tub2 sequence of strains NFE1000 and NFE1002 was identical along its aligned length to the amplified tub2 sequence of strain NFE1001 (SEQ ID NO:10) and the beta tubulin (tub2) copy 2 gene (Moon et al., 2004; GenBank accession AY137611; SEQ ID NO: 12), differing from SEQ ID NO:8, SEQ ID NO:9, and SEQ ID NO: 11. FIG. 2 shows an alignment of some of these sequences. Comparison of tef1 amplified sequences (SEQ ID NO:13-14) for instance with GenBank Accessions AF457502 of E. elymi (SEQ ID NO:15) and AF457506 of E. amarillans (SEQ ID NO: 16) supported similar phylogenetic conclusions.

BLASTN analysis of each tef1 and tub2 allele indicated that the likely ancestral genomes of the NFE isolates were E. elymi and E. amarillans (which is typically found as an endophyte of Aveneae). Maximum parsimony trees for the tub2 and tef1 genes (data not shown) grouped the NFE isolates with E. amarillans (copy 1) and E. elymi (copy 2). These data indicate that the NFE endophytes are the result of interspecific hybridizations between E. amarillans and E. elymi. Based on this as well as their observed lack of production of sexual fruiting structures such as stroma, or ascospores, these isolates are considered asexual, and thus do not "choke" CWR host plant flower development.

Example 3

Ergot Alkaloid Analysis

The presence of ergot alkaloids in endophyte-infected plant material was analyzed using the Phytoscreen® PT ergot alkaloid kit (Agrinostics, Watkinsville, Ga.), which detects the ergoline ring moiety common to ergot alkaloids by a competitive based ELISA. Ergovaline as well as biosynthetic intermediates may be detected by this ELISA assay. Freeze dried plant material (100 mg) was extracted and mixed gently for 3 hr. The extract was allowed to settle overnight at 4° C., and a 1 mL sample was removed and centrifuged at 8000 rpm for 3 min. A 50 µL aliquot was assayed for ergot alkaloids according to the manufacturer's instructions.

Two endophyte-infected plants from each NFE group were tested. The analysis of the CWR plants showed that the ergot alkaloid levels of five plants were very low, ranging from 1.4-66 ppb (close to the lowest level of detection), but with one plant showing a level of 477 ppb, a level similar to that of Kentucky 31 endophyte-infected tall fescue grass (365-<2000 ppb ergot alkaloids) sampled at the same time. Additional sampling and HPLC analysis was performed to confirm the level of ergot alkaloid accumulation in such plants.

Figure 3A:
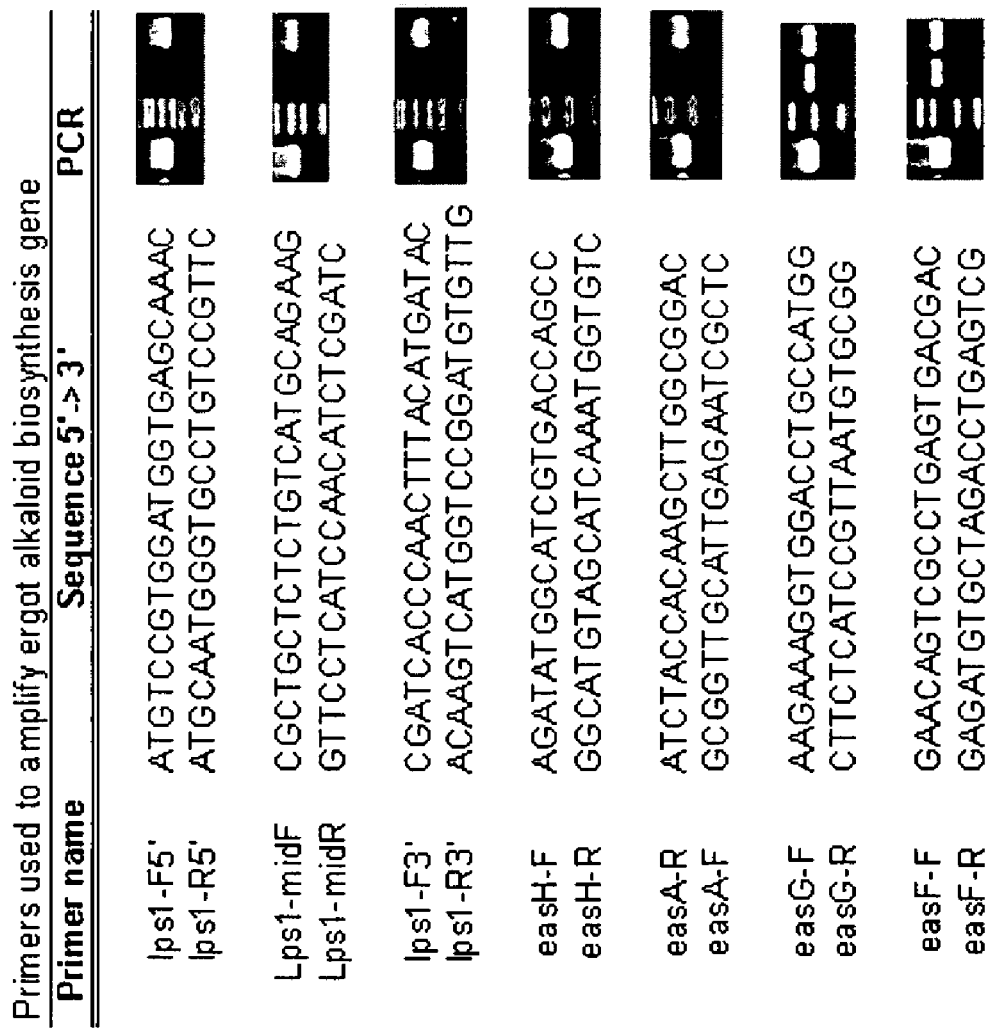
FIG. 3A-3D. Result from PCR amplification of *Neotyphodium* gene sequences specifying ergot alkaloid synthesis (FIG. 3A, using SEQ ID NOs: 20-33), loline biosynthesis (FIG. 3B, using SEQ ID NOs: 34-51), peramine biosynthesis (FIG. 3C, using SEQ ID NOs: 52-57), or lolitrem (indole-diterpene) biosynthesis (FIG. 3D, using SEQ ID NOs: 58-77).

Table 2 shows the result of an analysis of ergot alkaloid production by several CWR host line—fungal symbiont combinations. ELISA was performed using the Agrinostics Phytoscreen© PT ergot alkaloid kit (Agrinostics, Watkinsville, Ga.). HPLC was performed essentially as per Panaccione et al. (2003). Endophyte presence and presence of specific sequences related to fungal metabolite production was determined by PCR (see also Example 1 and also FIG. 3A-3D), using PCR conditions essentially as per Example 1. The results of Table 2 and in FIG. 3A confirm that, for the ergot alkaloids (anti-herbivore), asexual isolate NFE1001 lacks sequences corresponding to several genes in the ergot biosynthetic pathway, and is unable to synthesize the herbicide-toxic alkaloid ergovaline and several other precursor compounds. Instead, it accumulates chanoclavine. The other tested asexual isolates contain the ergot biosynthetic genes and can synthesize ergovaline.

Figure 3B:
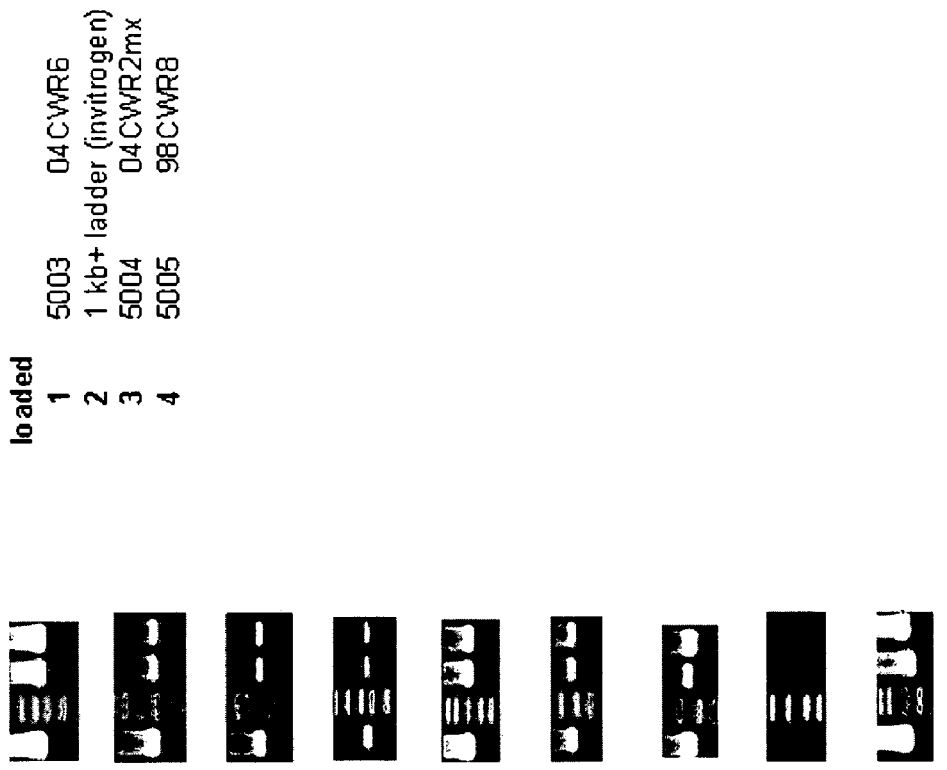
Figure 3C:
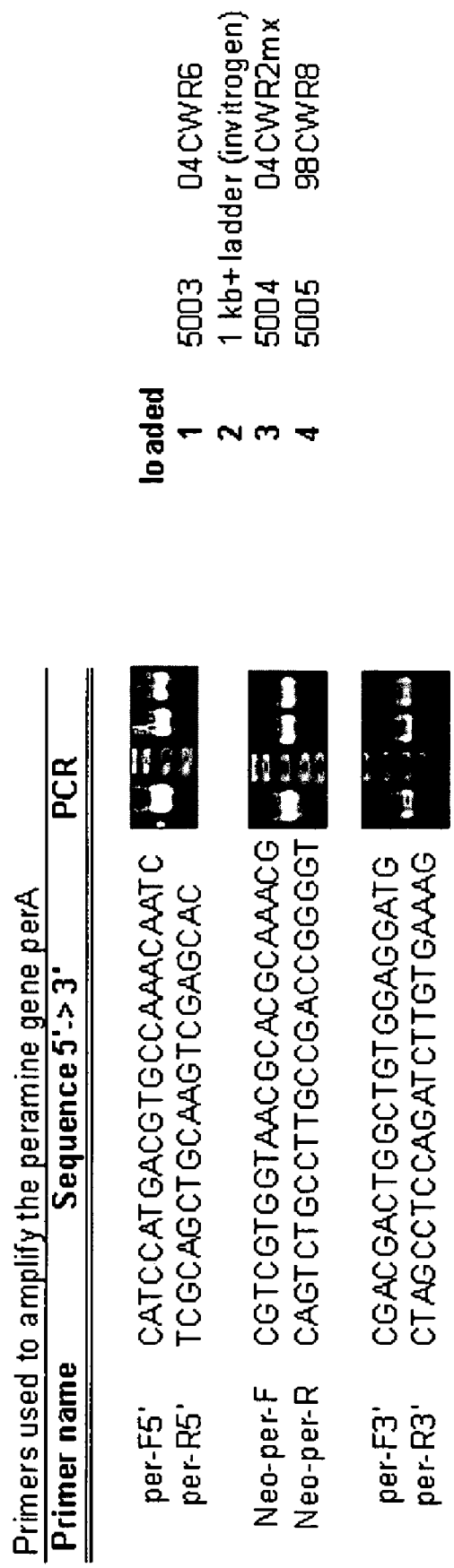
Figure 3D:
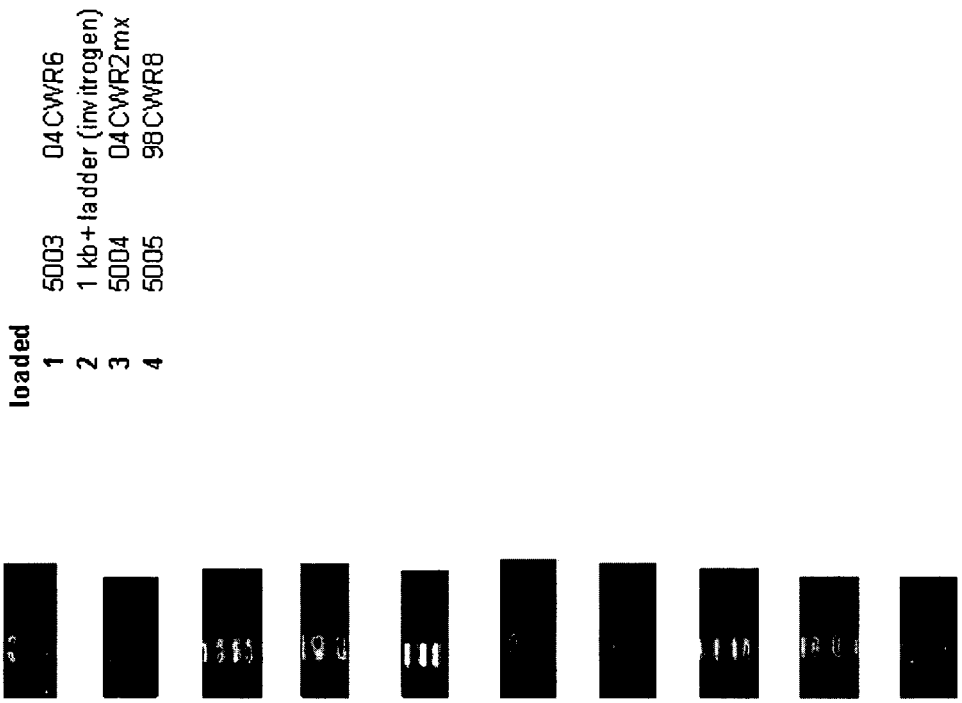

Regarding the loline alkaloids (anti-insect), all but the penultimate pathway gene, lolP, are present as seen in FIG. 3B, suggesting that the genes encoding the loline synthetic pathway are derived from the fungal isolates' E. amarillans parent, as a similar result is found with these isolates. Thus these isolates cause accumulation of N-methylloline. The isolates were also tested for ability to synthesize peramine, an anti-insect alkaloid. Based on the PCR result of FIG. 3C, all isolates are expected to synthesize peramine. FIG. 3D indicates that none of the isolates comprise sequences corresponding to intact genes for indole-diterpene (anti-herbivore) compounds. Thus, none of the isolates would be expected to synthesize indole-diterpenes, and the livestock palatability of combinations of CWR with such isolates would be enhanced relative to CWR plants colonized by endophytes that synthesize indole-diterpenes.

TABLE 2

Summary of Ergot Alkaloid Analysis by ELISA and HPLC

| | | | | ELISA | | HPLC (µg/g of tissue) | | | |
| --- | --- | --- | --- | --- | --- | --- | --- | --- | --- |
| Sample | plant background | Endophyte ID | Endophyte status | ELISA result | ppb (×80) | ergovaline | 6,7-secolysergic acid | Chanoclavine | agroclavine lysergic acid lysergyl alanine |
| CWR08 | 04CWR6 | | − | 3.2 | 256.0 | nd | nd | nd | nd |
| CWR11 | 04CWR6 | | − | 4.7 | 376.0 | nd | nd | nd | nd |
| CWR26 | 04CWR6 | NFE1000/5003 | + | 8.6 | 688.0 | 0.11 | nd | nd | nd |
| CWR16 | 04CWR6 | NFE1000/5003 | + | 7.2 | 576.0 | 0.21 | nd | nd | nd |
| CWR19 | 04CWR6 | NFE1000/5003 | + | 25+ | 2000.0 | 0.33 | ~0.01 | nd | nd |
| CWR23 | 04CWR6 | NFE1000/5003 | + | 18.2 | 1456.0 | 0.19 | ~0.01 | nd | nd |
| CWR24 | 04CWR6 | NFE1000/5003 | + | 7.4 | 592.0 | 0.11 | ~0.02 | nd | nd |
| CWR12 | 98CWR8 | | − | 2.9 | 232.0 | nd | nd | nd | nd |
| CWR01 | 98CWR8 | NFE1002/5005 | + | 12.8 | 1024.0 | 0.25 | 0.06 | nd | nd |
| CWR05 | 98CWR8 | NFE1002/5005 | + | 4.7 | 376.0 | 0.12 | 0.03 | nd | nd |
| CWR29 | 98CWR8 | NFE1002/5005 | + | 16.8 | 1344.0 | 0.37 | 0.03 | nd | nd |
| CWR06 | 04CWR2MX | | − | 2.8 | 224.0 | nd | nd | nd | nd |
| CWR14 | 04CWR2MX | NFE1001/5004 | + | 25+ | 2000.0 | nd | 0.26 | 33.22 | nd |
| CWR15 | 04CWR2MX | NFE1001/5004 | + | 25+ | 2000.0 | nd | 0.17 | 24.36 | nd | nd = not detected

Example 4

CWR-*Neotyphodium* Combination Cultivar Development and Breeding Program

*Neotyphodium* strains of the present invention are introduced into CWR plants of varying genotypes and geographic origin, lacking such endophytic fungi, to create plant-endophyte combinations with improved agronomic characteristics, analogously to the method of Bouton et al., 2002. Thus, given CWR-*Neotyphodium* combinations may be created and selected in a breeding/cultivar development program based on their ability to form and maintain a mutualistic combination that results in an agronomic benefit. Rating of agronomic characteristics of the combination may also be utilized in such a breeding program. These characteristics may include, without limitation, drought tolerance, biomass accumulation, resistance to insect infestation, palatability to livestock (e.g. herbivores), ease of reproduction, and seed yield, among others. Such combinations may differ in levels of accumulation of insect-toxic or herbicide-toxic fungal metabolites including ergot alkaloid levels, loline levels, peramine levels, or lolitrem levels, while displaying desired agronomic characteristics of CWR, including resistance to insect feeding or infestation, resistance to abiotic stress, palatability to livestock, biomass accumulation, ease of reproduction, and seed yield, among other traits.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 6,111,170

U.S. Patent Publications 20060121593; 20060150273

Bouton J H, Latch G C M, Hill N S, Hoveland C S, McCann M A, Watson R H, Parish J A, Hawkins L L, Thompson F N, 2002. Reinfection of tall fescue cultivars with non-ergot alkaloid-producing endophytes. *Agronomy Journal* 94: 567-574.

Bultman T L, White J F, 1988. "Pollination" of fungus by a fly. *Oecologia* 75: 317-9.

Christensen M J, Leuchtmann A, Rowan D D, Tapper B A, 1993. Taxonomy of *acremonium* endophytes of tall fescue (*Festuca arundinacea*), meadow fescue (*F. pratensis*) and perennial rye-grass (*Lolium perenne*). *Mycological Research* 97: 1083-92.

Clark E M, White, J F, and Patterson, R M, 1983. Improved histochemical techniques for the detection of *Acremonium coenophialum* in tall fescue and methods for in vitro growth of the fungus. *J. Microbiol. Methods* 1:149-155.

Clay K, Schardl C, 2002. Evolutionary origins and ecological consequences of endophyte symbiosis with grasses. *The American Naturalist* 160s: S99-S127.

Craven K D, Hsiau P T W, Leuchtmann A, Hollin W, Schardl C L, 2001. Multigene phylogeny of epichloë species, fungal symbionts of grasses. *Annals of the Missouri Botanical Garden* 88: 14-34.

Damrongkool P, Sedlock A B, Young C A, Johnson R D, Goetz K E, Scott B, Schardl C L, Panaccione D G, 2005. Structural analysis of a peptide synthetase gene required for ergopeptine production in the endophytic fungus *Neotyphodium lolii*. *DNA Sequence* 16: 379-85.

Fleetwood D J, Scott B, Lane G A, Tanaka A, Johnson R D, 2007. A complex ergovaline gene cluster in *Epichloe* endophytes of grasses. *Appl. Env. Microbiol.* 73: 2571-2579.

Ganley A R D, Scott B, 2002. Concerted evolution in the ribosomal RNA genes of an epichloë endophyte hybrid: Comparison between tandemly-arranged rDNA and dispersed 5S rrn genes. *Fungal Genetics & Biology* 35: 39-51.

Moon C D, Craven K D, Leuchtmann A, Clement S L, Schardl C L, 2004. Prevalence of interspecific hybrids amongst asexual fungal endophytes of grasses. *Molecular Ecology* 13: 1455-67.

Moon C D, Miles C O, Jarlfors U, Schardl C L, 2002. The evolutionary origins of three new *Neotyphodium* endophyte species from grasses indigenous to the southern hemisphere. *Mycologia* 94: 694-711.

Moon C D, Scott B, Schardl C L, Christensen M J, 2000. The evolutionary origins of epichloë endophytes from annual ryegrasses. *Mycologia* 92: 1103-18.

Moon C D, Tapper B A, Scott B, 1999. Identification of epichloë endophytes in planta by a microsatellite-based PCR fingerprinting assay with automated analysis. *Applied and Environmental Microbiology* 65: 1268-79.

Panaccione D G, Tapper B A, Lane G A, Davies E, Fraser K., 2003. Biochemical outcome of blocking the ergot alkaloid pathway of a grass endophyte. *J. Agric. Food Chem.* 51: 2003.

Panaccione D G, 2005. Origins and significance of ergot alkaloid diversity in fungi. *FEMS Microbiol. Lett.* 251: 9-17.

Schardl C L, Craven K D, 2003. Interspecific hybridization in plant-associated fungi and oomycetes: A review. *Molecular Ecology* 12: 2861-73.

Schardl C L, Leuchtmann A, 1999. Three new species of epichloë symbiotic with North American grasses. *Mycologia* 91: 95-107.

Schardl C L, Leuchtmann A, Tsai H-, Collett M A, Watt D M, Scott D B, 1994. Origin of a fungal symbiont of perennial ryegrass by interspecific hybridization of a mutualist with the ryegrass choke pathogen, *Epichloë typhina*. *Genetics* 136: 1307-17.

Siegel M R, Latch G C M, Bush L P, Fannin F F, Rowan D D, Tapper B A, Bacon C W, Johnson M C, 1990. Fungal endophyte-infected grasses: Alkaloid accumulation and aphid response. *Journal of Chemical Ecology* 16: 3301-15.

Spiering M J, Moon C D, Wilkinson H H, Schardl C L, 2005. Gene clusters for insecticidal loline alkaloids in the grass-endophytic fungus *Neotyphodium uncinatum*. *Genetics* 169: 1403-14.

Spiering M J, Wilkinson H H, Blankenship J D, Schardl C L, 2002. Expressed sequence tags and genes associated with loline alkaloid expression by the fungal endophyte *Neotyphodium uncinatum*. *Fungal Genetics and Biology* 36: 242-54.

Swofford D L, PAUP*. phylogenetic analysis using parsimony (*and other methods). Version 4.0. Sinauer Associates, Sunderland, Mass.

Tanaka A, Tapper B A, Popay A, Parker E J, Scott B, 2005. A symbiosis expressed non-ribosomal peptide synthetase from a mutualistic fun gal endophyte of perennial ryegrass confers protection to the symbiotum from insect herbivory. *Molecular Microbiology* 57: 1036-50.

Tsai H-, Liu J-, Staben C, Christensen M J, Latch G C M, Siegel M R, Schardl C L, 1994. Evolutionary diversification of fungal endophytes of tall fescue grass by hybridization with epichloë species. *Proceedings of the National Academy of Sciences (USA)* 91: 2542-6.

Vinton M A, Kathol E S, Vogel K P, Hopkins A A, 2001. Endophytic fungi in Canada wild rye in natural grasslands. *Journal of Range Management* 54: 390-395.

Wang J, Machado C, Panaccione D G, Tsai H-, Schardl C L, 2004. The determinant step in ergot alkaloid biosynthesis by an endophyte of perennial ryegrass. *Fungal Genetics & Biology* 41: 189-98.

White J F, Jr, Bultman T L, 1987. Endophyte-host associations in forage grasses. VIII. heterothallism in *Epichloë typhina*. *American Journal of Botany* 74: 1716-21.

White T J. Bruns T, Lee S. Taylor J. Amplification and direct sequencing of fungal ribosomal RNA genes for phylogenetics. In: Innis M A, Gelfand D H, Sninsky J J, White T J., editors. PCR protocols: a guide to method and applications. San Diego, Calif: Academic Press; 1996. pp. 315-322.

Young C A, Felitti S, Shields K, Spangenberg G, Johnson R D, Bryan G T, Saikia S, Scott B, 2006. A complex gene cluster for indole-diterpene biosynthesis in the grass endophyte *Neotyphodium lolii*. *Fungal Genetics and Biology* 43: 679-93.

What is claimed is:

1. An isolated *Neotyphodium* sp, endophyte selected from the group consisting of: NFE1000, NFE1001, and NFE1002, cultures of the endophyte having been deposited with NRRL accession numbers NRRL 50005, NRRL 50004, and NRRL 50003, respectively.

2. A synthetic combination of the endophyte of claim 1 and a host plant.

3. The synthetic combination of claim 2, wherein said host plant is a host grass plant.

4. The synthetic combination according to claim 3, wherein:
   a) the host grass plant displays at least equivalent reproductive vigor as a host grass plant identical except for the absence of the endophyte, when compared under identical conditions;
   b) the endophyte protects the host grass plant from biotic and/or abiotic stresses; and
   c) the host grass plant or a parental generation of the host grass plant is artificially inoculated with the endophyte.

5. The synthetic combination of claim 2, wherein the host plant is an *Elymus canadensis* host plant.

6. The synthetic combination of claim 4, wherein the synthetic combination is achieved by introduction of the endophyte to the host grass plant by a method selected from the group consisting of: inoculation, infection, grafting, and seed transmission.

7. The synthetic combination of claim 4 wherein the abiotic stress is selected from the group consisting of: water deficiency, nutrient deficiency, heat stress, salt toxicity, aluminum toxicity, and freezing temperatures.

8. The synthetic combination of claim 4 wherein the biotic stress is selected from the group consisting of: insect infestation, nematode infestation, and herbivore grazing.

9. Seed of a host grass plant comprising a synthetic combination of the endophyte of claim 1 with said host grass plant.

10. A method for propagating an *Elymus canadensis*-*Neotyphodium* sp. combination, comprising:
   a obtaining a *Elymus canadensis* host grass plant comprising the synthetic combination of claim 5; and
   b harvesting seed from the plant; the plant or a parental generation of the plant having been inoculated with said endophyte, or said endophyte having been introduced into a parental generation of the plant through crossing and/or backcrossing procedures.

11. A method for enhancing the growth or reproduction of an *Elymus canadensis* host grass plant in the presence of a biotic or abiotic stress, comprising: contacting the host grass plant with a strain of endophyte of *Neotyphodium* sp., selected from the group consisting of: NFE1000, NFE1001, and NFE1002, cultures of the endophyte having been deposited with NRRL accession numbers: NRRL 50005, NRRL 50004, and NRRL 50003, respectively, such that the endophyte colonizes the plant.

12. The method of claim 11, wherein the host grass plant has enhanced root growth, more tillers, enhanced total biomass, or enhanced seed yield in comparison to an otherwise identical host grass plant lacking said endophyte.

13. The method of claim 11, wherein the stress is a biotic stress caused by at least one organism selected from the group consisting of an herbivore, a nematode, and an insect.

14. The method of claim 13, wherein the insect to which increased resistance is conferred on the host grass plant is selected from the group consisting of: fall armyworm and Russian wheat aphid.

15. The method of claim 11, wherein colonization of the host grass plant is achieved by introduction of the endophyte to the host grass plant by a method selected from the group consisting of: inoculation, infection, grafting, seed transmission, and combinations thereof.

16. The method of claim 11, wherein said biotic stress is a pest stress or an insect stress.

17. A method for propagating an *Elymus canadensis*-*Neotyphodium* sp. combination, comprising:
   vegetatively reproducing *Elymus canadensis* plant tissue colonized by the synthetic combination of claim 5.

18. The method of claim 11, wherein said abiotic stress is a water deficit stress.

* * * * *

UNITED STATES PATENT AND TRADEMARK OFFICE
CERTIFICATE OF CORRECTION

PATENT NO. : 7,892,813 B2  
APPLICATION NO. : 12/029797  
DATED : February 22, 2011  
INVENTOR(S) : Young et al.

Page 1 of 1

It is certified that error appears in the above-identified patent and that said Letters Patent is hereby corrected as shown below:

In claim 1, column 43, line 26, delete "sp," and insert --sp.--.

Signed and Sealed this  
Twentieth Day of September, 2011

David J. Kappos  
*Director of the United States Patent and Trademark Office*